United States Patent [19]

Rodak et al.

[11] Patent Number: 5,071,052
[45] Date of Patent: Dec. 10, 1991

[54] SURGICAL FASTENING APPARATUS WITH ACTIVATION LOCKOUT

[75] Inventors: Daniel P. Rodak, Milford; Ernest Aranyi, Easton, both of Conn.

[73] Assignee: United States Surgical Corporation, Norwalk, Conn.

[21] Appl. No.: 598,800

[22] Filed: Oct. 15, 1990

Related U.S. Application Data

[63] Continuation of Ser. No. 247,939, Sep. 22, 1988, abandoned.

[51] Int. Cl.⁵ .................................................. A61B 17/072
[52] U.S. Cl. ........................................ 227/178; 227/8; 227/19; 227/124
[58] Field of Search ............... 227/175, 176, 180, 182, 227/8, 19, 20, 124, 152, 153, 178

[56] References Cited

U.S. PATENT DOCUMENTS

| | | | |
|---|---|---|---|
| 3,494,533 | 2/1970 | Green et al. | 227/19 |
| 3,665,924 | 5/1972 | Noiles et al. | 128/305 |
| 3,675,688 | 7/1972 | Bryan et al. | 227/19 |
| 3,692,224 | 9/1972 | Astafiev et al. | 227/19 |
| 3,735,762 | 5/1973 | Bryan et al. | 128/305 |
| 3,780,416 | 12/1973 | Rider | 29/212 D |
| 3,844,289 | 10/1974 | Noiles | 128/334 R |
| 3,873,016 | 3/1975 | Fishbein | 227/83 |
| 3,955,581 | 5/1976 | Spasiano et al. | 128/334 R |
| 4,086,926 | 5/1978 | Green et al. | 128/33 R |
| 4,256,251 | 3/1981 | Moshofsky | 227/120 |
| 4,354,628 | 10/1982 | Green | 227/19 |
| 4,372,316 | 2/1983 | Blake, III et al. | 128/325 |
| 4,383,634 | 5/1983 | Green | 227/19 |
| 4,391,401 | 7/1983 | Moshofsky | 227/19 |
| 4,500,025 | 2/1985 | Skwar | 227/19 |
| 4,508,253 | 4/1985 | Green | 227/19 |
| 4,520,817 | 6/1985 | Green | 227/19 |
| 4,527,724 | 7/1985 | Chow et al. | 227/8 |
| 4,530,453 | 7/1985 | Green | 227/19 |
| 4,556,058 | 12/1985 | Green | 128/305 |
| 4,568,009 | 2/1986 | Green | 227/19 |
| 4,576,165 | 3/1986 | Green et al. | 128/305 |
| 4,576,167 | 3/1986 | Noiles | 227/19 |
| 4,591,085 | 5/1986 | DiGiovanni | 227/8 |
| 4,597,517 | 7/1986 | Wagdy | 227/8 |
| 4,605,004 | 8/1986 | DiGiovanni et al. | 227/176 |
| 4,612,933 | 9/1986 | Brinkerhoff et al. | 227/19 |
| 4,633,861 | 1/1987 | Chow et al. | 128/305 |
| 4,646,745 | 3/1987 | Noiles | 227/19 |
| 4,664,305 | 5/1987 | Blake, III et al. | 227/19 |
| 4,715,520 | 12/1987 | Roehr, Jr. et al. | 227/19 |
| 4,809,898 | 3/1989 | Gassner et al. | 227/8 |
| 4,892,244 | 1/1990 | Fox et al. | 227/8 |

FOREIGN PATENT DOCUMENTS

1580725  9/1969  France ................................ 227/176

Primary Examiner—Frank T. Yost
Assistant Examiner—Rinaldi Rada
Attorney, Agent, or Firm—Thomas R. Bremer; Peter G. Dilworth; Rocco S. Barrese

[57] ABSTRACT

A surgical fastener, such as a stapler, is constructed of a pair of opposed jaws, one of which comprises an anvil and the other of which holds the fastener holder assembly, such as a cartridge, oriented towards the anvil. A clamp bar operable by a lever is longitudinally displaceable to advance the cartridge towards the anvil to clamp the subject matter prior to fastening. The clamp bar rides within a frame which supports the lever and the jaws. A thrust bar is longitudinally displaceable in response to the pivoting of a trigger to operate staple pushing elements within the cartridge to eject the fasteners towards the anvil for engagement with body tissue to be fastened. The thrust bar rides within the clamp bar. A pin is inserted between ends of the jaws to secure the jaws against loss of any portion of the body tissue during the clamping procedure. The pin has a cam surface which moves during a securing of the pin. A lockout system is provided for preventing both clamping and ejection of the fasteners, e.g., staples, until the pin is secured. The lockout system includes a bell crank which blocks movement of the clamp bar during an unsecured state, the crank being operated by a cam follower which rides on the cam surface of the pin. An intermediate link connects the trigger with the thrust bar, the intermediate link riding on the lever to be retracted during blockage of the clamp bar so as to prevent operation of the thrust bar.

12 Claims, 4 Drawing Sheets

SURGICAL FASTENING APPARATUS WITH ACTIVATION LOCKOUT

This is a continuation of copending application Ser. No. 07/247,939 filed on Sep. 22, 1988, now abandoned.

BACKGROUND OF THE INVENTION

This invention relates to a surgical fastening apparatus which applies a plurality of fasteners simultaneously or substantially simultaneously and more particularly to such a surgical stapler provided with a lockout system for inhibiting activation of the stapler.

Cartridge type staplers are frequently employed in surgical procedures, such as for the stapling of a section of intestine or other body tissues. In a common form of cartridge, staples are arranged in an array of rows and columns. The array of staples, upon being dispensed to the body tissue, can close off the tissue, or other subject matter to be stapled, in a manner similar to stitching, but with a great saving of time. In these types of staplers, one jaw member comprises an anvil for bending the legs of the staples, and the other jaw member includes a cartridge containing the staples. Examples of such cartridge type surgical staplers are found, for example, in U.S. Pat. No. 4,568,009, U.S. Pat. No. 4,530,453, U.S. Pat. No. 4,508,253, U.S. Pat. No. 4,383,634, U.S. Pat. No. 4,354,628 and U.S. Pat. No. 3,494,533.

In the utilization of a surgical stapler having a U-shaped jaw configuration, correct practice requires that a lock pin be secured across the jaw members, so as to contain the body tissue between the jaw members before advancement or adjustment of the cartridge toward the anvil. The lock pin ensures among other things) that upon a compression of the body tissue by advancement of the cartridge towards the anvil, the tissue remains in the space between the two jaw members, namely, the anvil and the cartridge. Subsequently, after the gap between the anvil and the cartridge has been adjusted or closed to the required spacing, push bars within the cartridge are advanced by a suitable actuator mechanism of the stapler to urge the staples out of the cartridge, into the tissue, and against a corresponding set of channels in the anvil to bend the legs of the staples in response to advancement of the push bars. It is noted that throughout this procedure the lock pin is connected between the jaws.

A problem arises, however, that in the past it has been possible to operate these types of staplers without placement of the lock pin between the cartridge holding jaw member and the anvil jaw. Thus, there was the possibility that, in haste, a surgeon may fail to properly place the lock pin between the jaw members so that during clamping of the tissue or firing of the instrument the compression forces produced could displace some of the tissue from between the jaw members or cause the jaw members themselves to become misaligned resulting in improperly formed staples or incomplete stapling of the tissue.

SUMMARY OF THE INVENTION

The foregoing problems are overcome and other advantages are provided herein an apparatus for applying surgical fasteners to body tissue comprising: a first jaw member comprising an anvil assembly; a second jaw member comprising a fastener holding assembly movably mounted relative to said anvil assembly; actuator means for moving the fastener holding assembly toward the anvil assembly to clamp the tissue to be fastened between the anvil assembly and the fastener holding assembly; pin means for securing and second jaw members, said pin means providing a secured state and an unsecured state; activation means to eject fasteners from said fastener holding assembly in a direction toward said anvil assembly; and lockout means driven by said pin means for inhibiting operation of said actuator means and said activation means while in said unsecured state, said lockout means permitting operation of said actuator means and said activation means during said secured state.

It is an object of the invention to prevent deliberate or inadvertent closing of the jaw members or the firing of the staples until after the lock pin has been properly secured. This object is met by the present invention by the provision of a lockout system for inhibiting the advancement of the jaw members and the firing of the staples until after the lock pin has been secured.

In one embodiment of the construction of the present stapler, both jaw members are oriented in a U-shaped configuration at one end of the frame and a jaw member adjusting means, a stapler activating means and a handle being provided at the opposite end of the frame. A actuator assembly is located within the frame and connects the cartridge with the stapler activating means. The actuator assembly comprises an outer clamp bar and an inner thrust bar, the thrust bar being located within the clamp bar and translatable relative to the clamp bar. Upon activation of the adjusting means, the clamp bar advances along the frame to push the cartridge towards the anvil. Upon activation of the trigger, the thrust bar advances into the cartridge to dispense the staples.

In accordance with a feature of the invention, the lock pin, after being placed in position across the jaws, is locked in position by a rotation of the pin about its axis. The pin is provided with a cam surface which, by means of a cam follower, is operatively connected to a lock which inhibits movement of the actuator assembly.

In accordance with a further feature of the invention, an intermediate link is connected between the stapler activating means and the thrust bar for mechanically coupling the stapler activating means to the thrust bar for dispensing the staples. The intermediate link is carried by the clamp bar by means of a pin and slot arrangement which results in an insertion and an extraction of the intermediate link upon a pivoting of the adjustment means. When the stapler jaws are open, this being prior to advancement of the cartridge towards the anvil, the position of the adjustment means is such that the intermediate link is disengaged from the thrust bar and from the stapler activating means. Upon advancement of the cartridge and the clamp bar by activation of the adjustment means, the intermediate link is brought into a position of engagement between the staple thrust bar and the staple activating means. Thusly, the stapler activating means can advance the thrust bar for firing the staples only after the clamp bar has advanced with the cartridge to adjust the gap size to the proper dimension for stapling. In this way, a lockout of the clamp bar which inhibits motion of the clamp bar also prevents activation of the thrust bar. The pin operated lock is effective to prevent motion of both the clamp bar and the thrust bar.

BRIEF DESCRIPTION OF THE DRAWING

The aforementioned aspects and other features of the invention are explained in the following description, taken in conjunction with the accompanying drawing wherein.

DETAILED DESCRIPTION

With reference to FIGS. 1-4, there is shown a stapler 20 incorporating the pin-operated lockout system of the invention. The stapler 20 comprises an anvil assembly 22 and a cartridge holder 24 supported at one end of an elongated frame 26. A manually operated adjustment lever 28 and a manually operated stapler activating means, e.g., trigger 30 are located with a handle 32 at an end of the frame 26 opposite the anvil 22. A staple cartridge 34 is slidably disposed within the holder 24. The holder 24 with the movable cartridge 34 constitute a movable jaw member of the stapler 20, and the anvil 22 constitutes a fixed jaw member of the stapler 20. Material to be stapled, such as a body tissue 36, indicated in phantom, is placed in a gap 38 formed by the two jaw members prior to a stapling operation of the stapler 20. By way of example, the body tissue 36 may be a portion of intestine which is readily inserted between the jaw members in a procedure for tying off a section of the intestine by a stapling operation. As will be described hereinafter, means are provided for advancing the cartridge 34 towards the anvil assembly 22, this operation constituting an adjustment of the jaw members which squeezes the tissue 36 until the gap 38 is adjusted to a predesignated size for ejection of staples from the cartridge 34. The stapler 20 further comprises a pin assembly 40 having a pin 42 which is advanced manually by means of a knob 44 from the holder 24 into an end portion of the anvil assembly 22. Pin 42 is rotated with said knob 44 to a locked position to retain the subject matter, such as the tissue 36, between the cartridge 34 and the anvil assembly 22 during an adjustment of the gap 38. The pin 42, thereby, secures the jaws of the stapler 20 against loss of subject matter and misalignment of jaw members during a stapling procedure.

In the ensuing description with reference to FIGS. 1-4, the frame 26 will be described as a box frame having four sides for convenience in showing locations and operations of various components of the stapler 20. It is to be understood, however, that to facilitate manufacture of the stapler 20, it has been found practicable in the construction of a preferred embodiment of the invention to employ a frame 46, as will be described with reference to FIG. 5, having two side members 48 and 50 which support components of the stapler.

Figure 1:
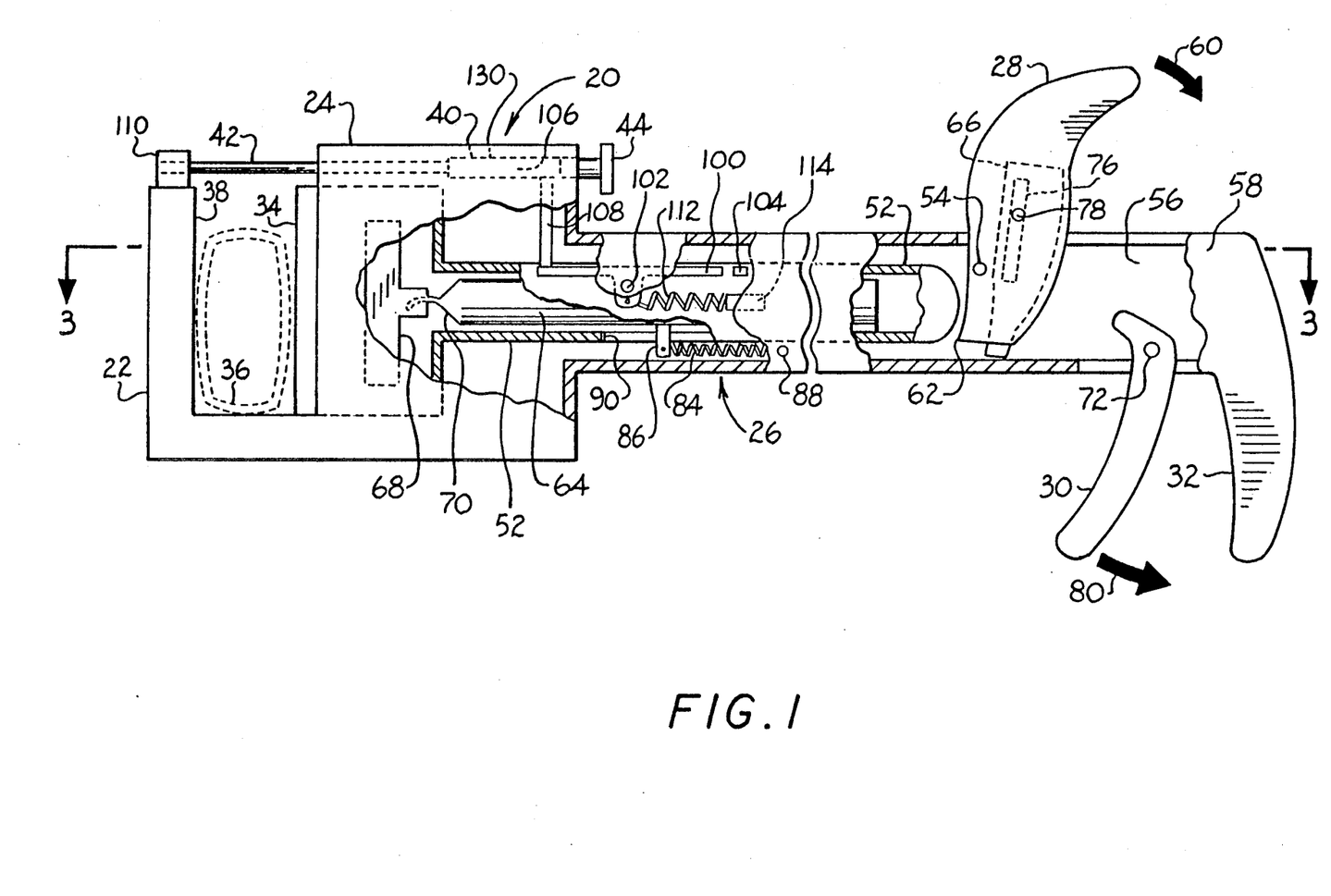
FIG. 1 is a side elevation view of a stapler including the lockout system of the invention, the view being partially cutaway to show interior components of a stapling mechanism, the view being partially stylized to facilitate description of the operation of the stapler, the stapler being shown prior to initiation of a clamping procedure.

The cartridge 34 is mechanically connected via a clamp bar 52 to the adjustment lever 28. The adjustment lever 28 is pivotally secured about a pivot 54 to the frame 26, the pivot 54 being formed as a pin which extends between sidewalls 56 and 58 of the frame 26 and passes through the adjustment lever 28. A pivoting of the lever 28 clockwise, in the direction of the arrow 60, causes a nose 62 of the lever 28 to push against the bar 52 to translate the bar 52 and the cartridge 34 connected thereto towards the anvil assembly 22 to clamp the body tissue 36 therebetween which in accordance with a feature of the present invention will only occur after pin assembly 40 has been advanced and secured.

Figure 2:
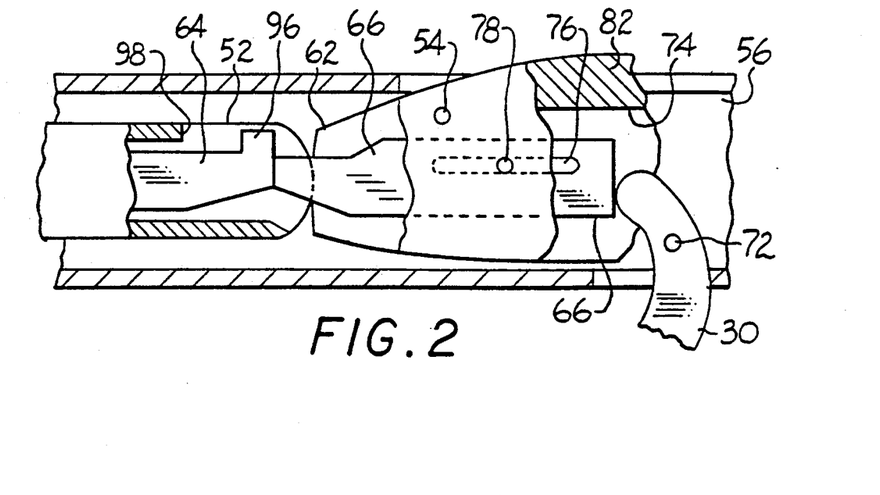
FIG. 2 is a sectional view of a portion of the stapler of FIG. 1 showing rotation of an adjustment lever to the clamping position.
Figure 3:
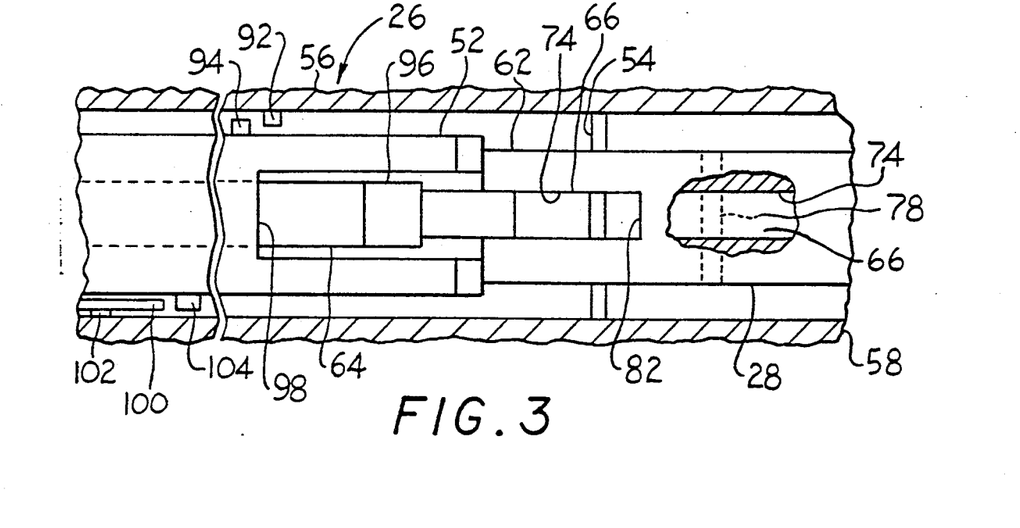
FIG. 3 is a top sectional view of a portion of the stapler taken along the line 3—3 in FIG. 1, the view showing the arrangement of mechanical components at the inception of a staple dispensing procedure.

The stapler 20 further comprises a thrust bar 64, which, in combination with an intermediate link 66, provides for mechanical connection between a staple pusher element 68 and the stapler activating means 30. The pusher element 68 is located within the cartridge 34 and, in a well-known fashion, dispenses staples by driving the staples outward through the tissue 36 towards the anvil assembly 22 upon a displacement of the element 68 towards the anvil assembly 22. As legs of the staples (not shown) press against grooves (not shown) in the anvil assembly 22, the legs are curved to grip the tissue 36. The thrust bar 64 connects by a hook arrangement 70 to the pusher element 68 and if desired could also connect to a knife blade assembly (not shown in the drawings), the hook arrangement 70 permitting a well-known pivoting of the cartridge 34 for extraction and replacement of the cartridge 34 for reloading the stapler 20 with staples. The back end of the thrust bar 64 abuts the front end of the link 66, as shown in FIGS. 2 and 3 for connection of the thrust bar 64 to the trigger 30, a nose of the trigger 30 abutting the back end of the link 66. The trigger 30 is pivotally mounted to the frame 26 by a pivot 72, the pivot 72 being formed as a pin which extends between the sidewalls 56 and 58 of the frame 26 and passes through the trigger 30.

In accordance with a feature of the lockout system of the invention, the intermediate link 66 is carried within a channel 74 of the adjustment lever 28. The link 66 is provided with a slot 76, and the lever 28 is provided with a pin 78 which extends transversely of the channel 74 and passes through the slot 76. See FIG. 7. The link 66 is slidably mounted with the channel 74, the slot 76 and pin 78 serving to retain the link 66 within the channel 74 during a sliding movement of the link 66 within the channel 74. By virtue of the construction of the assembly of the lever 28 and link 66 within the channel 74, the slot 76 and the pin 78, the lever 28 is able to transport the link 66 from a position of engagement between the thrust bar 64 and the trigger 30 to a position removed from both the thrust bar 64 and the trigger 30. Pivoting of the lever 28 in the clockwise direction thereby serves to insert the link 66 into an operating position for operatively connecting the trigger 30 to the thrust bar 64, while a pivoting of the lever 28 in the counterclockwise direction retracts the link 66 from the operative position between the thrust bar 64 and the trigger 30. The trigger 30 is ineffective for the dispensing of staples until after the pin assembly 40 has been properly secured, unlocking the clamp bar 52 and the lever 28 has been rotated clockwise to advance the clamp bar 52 for closing the gap 38 between the jaws, which rotation of the lever 28 simultaneously places the link 66 in its operative position.

The retracted position of the link 66 is shown in FIG. 1, while the operative position of the link 66 is shown in side view of FIG. 2 and in top plan view in FIG. 3. Upon placement of the intermediate link 6 in its operative position, and upon rotation of the trigger 30 in the counterclockwise direction, as indicated by arrow 80, the nose of the trigger 30 pushes the link 66 through the channel 74 towards the anvil assembly 22. As the link 66 slides in the forward direction towards the anvil assembly 22, the link 66 pushes the thrust bar 64 towards the anvil assembly 22 for operation of the pusher element 68 to dispense the staples. In the construction of the adjustment lever 28, the bottom portion of the channel 74, facing the trigger 30, is open to receive the trigger 30. The top portion of the channel 74 is partially closed off by a roof section 82 which joins sidewalls of the lever 28 to provide adequate physical strength to the lever 28.

Upon release of the trigger 30, the thrust bar 64 is urged backwards away from the anvil assembly 22 by a spring 84. The spring 84 connects to the thrust bar 64 by means of a tab 86 extending outward from the bar 64, and connects to the frame 26 by attachment to a pin 88 which extends transversely between the sidewalls 56 and 58. The tab 86 extends through a slot 90 in the clamp bar 52 to engage with the spring 84, the slot permitting the tab 86 to translate with the thrust bar 64 during the dispensing of staples at which time the clamp bar 52 stands stationary for clamping the body tissue 36. Action of the spring 84 in retracting the thrust bar 64 (and knife blade assembly, if employed) also pushes the intermediate link 66 to its rest position within the lever 28 and pushes the trigger 30 back to its rest position. Upon retraction of the link 66 to its rest position within the lever 28, the lever 28 is now ready to be rotated from the operative position of the link 66 (FIGS. 2 and 3) to the retracted position of the link 66 (FIG. 1).

The spring bar 84 is employed also to retract the clamp bar 52, upon a pivoting of the lever 28 to retract position, to retract the cartridge 34 and open the gap 38 in the stapler jaws. Retraction of the clamp bar 52 by the spring 84 is accomplished by locating the slot 90 such that the right end of the slot 90 (as viewed in FIG. 1) abuts the tab 86 when the thrust bar 64 is in the retracted position. Thereby, the spring 84 urges the tab 86 against the right end of the slot 90 to drag the clamp bar 52 back to the retract position. A pair of stops 92 and 94 (FIG. 3) may additionally be placed on a sidewall of the frame 26 and a sidewall of the clamp bar 52, respectively, to counteract the force of the spring 84 when the clamp bar 52 reaches the retract position. The stops 92 and 94 engage with each other to prevent further retraction of the clamp bar 52 when the bar 52 becomes fully retracted. To prevent excessive forward motion of the thrust bar 64 during a squeezing of the trigger 30, a tab 96 may be provided upstanding from the back end of the thrust bar 64 (FIGS. 2 and 3) for engagement with the front end of a slot 98 in the back end of the clamp bar 52.

In accordance with a further feature of the present invention, the lockout system includes a bell crank 100 (FIGS. 1, 3 and 4) which is pivotally mounted by a pivot 102 disposed on a sidewall of the frame 26, such as the sidewall 58. The right end of the bell crank 100, as viewed in FIGS. 1, 3, and 4, contacts a stop 104 projecting from a sidewall of the clamp bar 52 upon movement of the clamp bar 52 towards the anvil assembly 22. The contact between the crank 100 and the stop 104 occurs for a horizontal orientation of the crank 100 as portrayed in FIG. 1. Upon a tilting of the crank 100, as portrayed in FIG. 4, the right end of the crank 100 clears the path of the stop 104 to allow translation of the clamp bar 52 towards the anvil assembly 22. As will be described in further detail with reference to FIG. 5, the pin assembly 40 includes a cam 106 coupled by a follower 108 to the left end of the crank 100. Advancement of the pin 42 across the gap 38 and rotation of the knob 44 to proper orientation secures the end of the pin 42 in a lock 110 at the end of the anvil assembly 22. Such securing of the pin 42 ensures that the pin 42 will remain in position across the jaw members of the stapler 20 during a clamping of the body tissue 36 and during the subsequent advancing of staples. In the case of a knob shaped as shown by knob 44 in the drawings herein, the user is readily apprised of the locked position by the orientation of the knob itself although other means to apprise the user of the same condition, such as detents, may also be employed for this same purpose.

Figure 4:
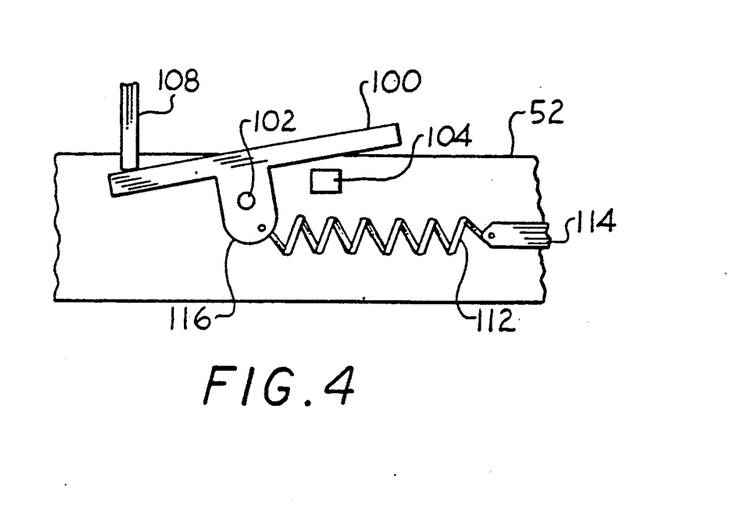
FIG. 4 is an enlarged fragmentary view of a cam operated bell crank for locking motion of a clamp bar, the view in FIG. 4 showing the unlocked and actuated position.

Upon rotation of the knob 44, a surface of the cam 106 slides past the upper end of the follower 108 to urge the follower 108 downward towards the crank 100 resulting in a tipping of the crank 100 as shown in FIG. 4. Thereby, the invention provides that, upon emplacement of the pin 42 across the stapler jaws, and upon subsequent rotation of the knob 44 to secure the pin 42 into place, the crank 100 is moved from the horizontal locking orientation to the inclined orientation which frees the clamp bar 52 for movement towards the anvil assembly 22. In the absence of the emplacement of the pin 42 across the stapler jaws and rotation of the knob 44, the crank 100 remains in the locked position to lock out movement of the clamp bar 52 so that no clamping of the body tissue 36 can take place. The lever 28 cannot be rotated clockwise because the lever nose 62 is blocked by the immovable clamp bar 52 and in the absence of the rotation of the lever 28 to the operative position of the intermediate link 66, the trigger 30 is ineffective to advance the thrust bar 64 for dispensing staples. A compression spring 112 connects between a tab 114 located on the frame sidewall 58 and a tang 116 of the crank 100 for urging the crank 100 against the follower 108 with a force which maintains pressure of the follower 108 upon a surface of the cam 106. Thereby, the crank 100 is constrained to follow the surface of the cam 106 so as to lock and unlock the stapler 20 in accordance with rotation of the knob 44 which in turn locks the pin into position. Thereby, the pin assembly 40 is operative to activate the stapler lockout system of the invention by preventing both the clamping of the body tissue 36 and the dispensing of staples thereby until the pin 42 has been properly secured.

Figure 5:
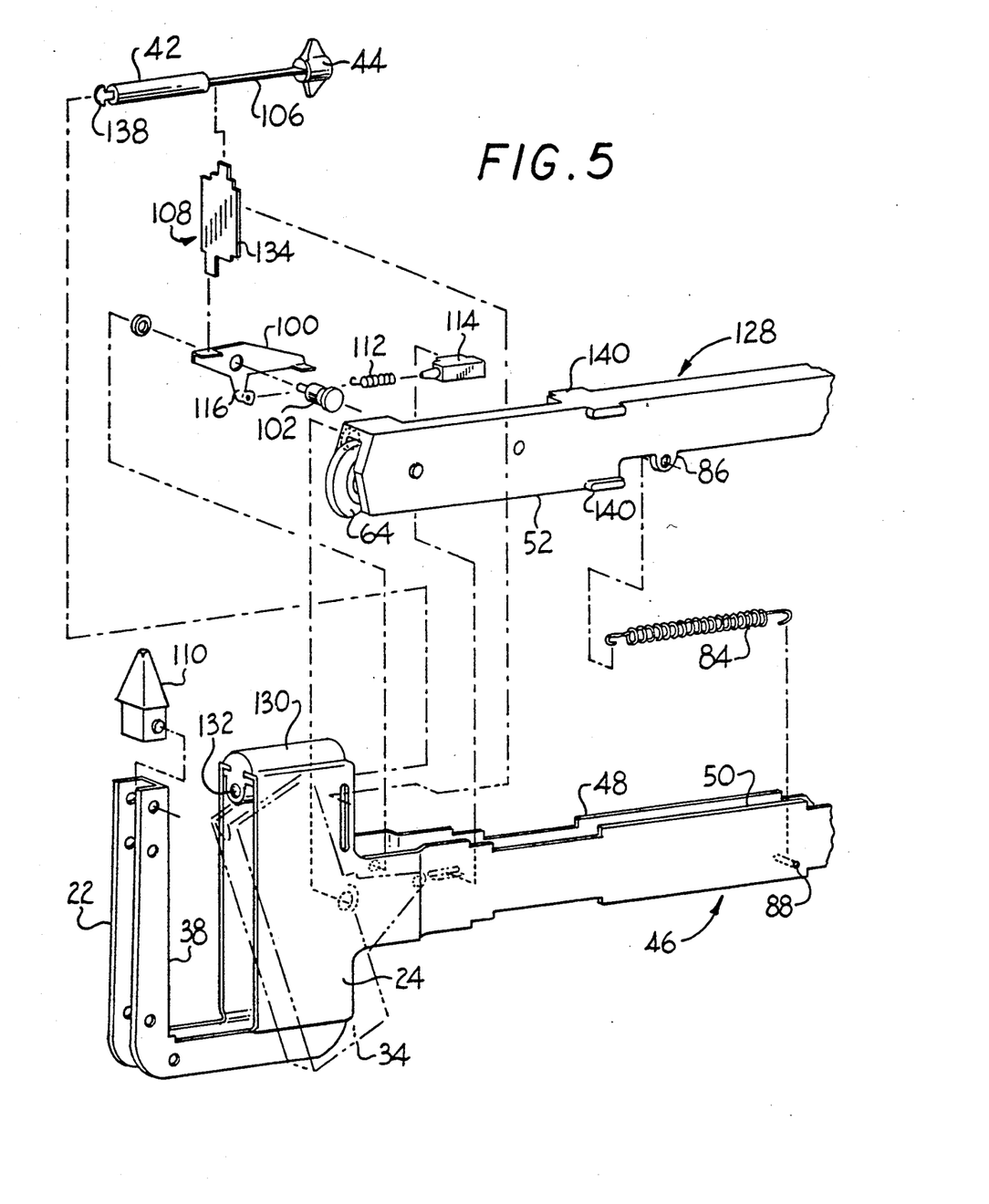
FIG. 5 is an exploded view of the stapler showing components employed in a construction of a preferred embodiment of the stapler.
Figure 6:
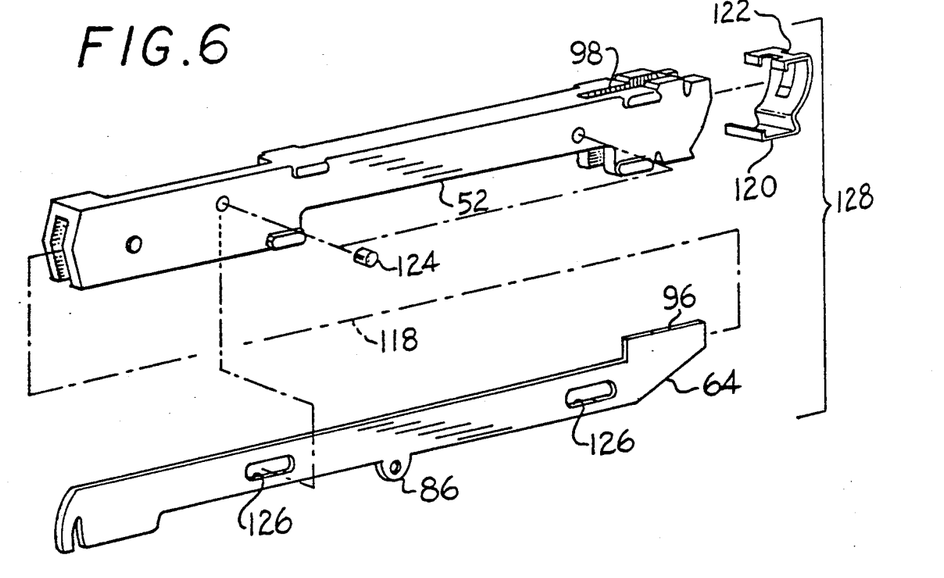
FIG. 6 shows components employed in the construction of a bar assembly of a preferred embodiment of the stapler.
Figure 7:
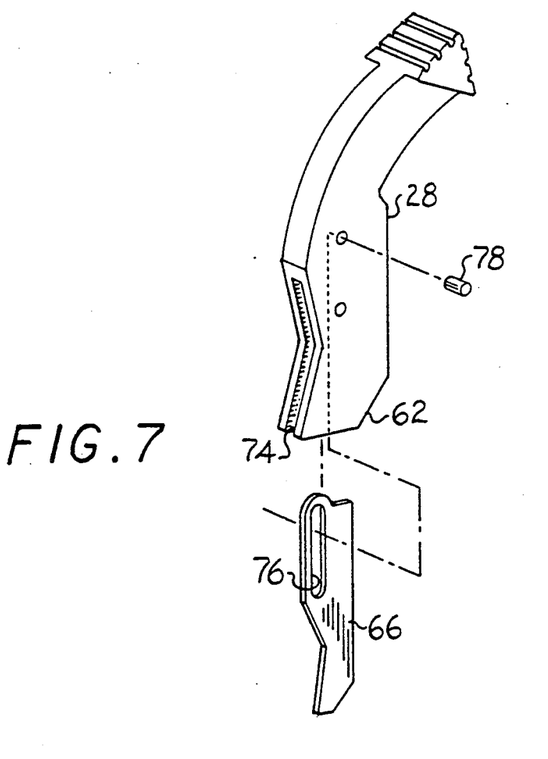
FIG. 7 shows an adjustment lever and an intermediate link of a staple dispensing mechanism carried by the adjustment lever as employed in a preferred embodiment of the stapler.

With reference also to FIGS. 5, 6 and 7, there are shown details in the construction of a preferred embodiment of the stapler 20. The thrust bar 64 is fabricated from an elongated section of a metallic plate, and is inserted within the clamp bar 52 as indicated by the construction line 118 in FIG. 6. The clamp bar 52 maybe fabricated of metal or plastic material, and is closed off by a cap 120 which fits to the back end of the bar 52 by spring tension. The cap 120 has a slot 122 which defines an entry port for the intermediate link 66. The thrust bar 64 is secured within the clamp bar 52, by means of pins 124 (one such pin shown in FIG. 6) secured within sidewalls of the clamp bar 52, and passing through slots 126 in the thrust bar 64. The pins 124 and the slots 126 permit translation of the thrust bar 64 relative to the clamp bar 52. The completed bar assembly 128 comprising the clamp bar 52 and the thrust bar 64 is located between the side members 48 and 50 of the arm 64 as shown by construction lines in FIG. 5.

The pin assembly 40 (FIG. 1) includes a housing 130 (FIG. 5) with a central bore 132 through which the pin 42 and the cam 106 are slidably mounted. As shown in FIG. 5, the pin has an outer circular cylindrical surface, the pin 42 being joined by the cam 106 to the knob 44. The cam 106 is in the form of a flat plate having a width much greater than its thickness so that, upon rotation of the cam 106 about a longitudinal axis of the pin 42, the follower 108 undergoes displacement as it rides on the surface of the cam 106. The follower 108 is constructed as a section of a plate which may be of metal, the follower 108 having an elongated tab 134 which rides within a slot of the cartridge holder 24, as illustrated by the appropriate connecting line in FIG. 5. The end of the pin 42 opposite the knob 44 terminates in a key 138 which engages in the lock 110 upon a sliding of the pin 42 along the bore 132 and across the gap 38 between the stapler jaws. Rotation of the pin 42 secures the key 138 in the lock 110 so as to retain the pin 42 in its position across the gap 38. Rotation of the knob 44 releases the key 138 from the lock 110 so as to permit withdrawal of the pin 42 from the anvil 22. The bar assembly 128 may be secured to the frame 46 by means of tabs 140 which ride upon edges of the side members 48 and 50.

By virtue of the foregoing construction and operation of the lockout system of the invention, the stapler can be safely used in a surgical procedure, and in other stapling situations, in which it is desired to close off a gap between stapler jaws by means of a pin prior to clamping the subject matter which is to be stapled. The locking system provides first for a securing of the pin across the gap of the stapler jaws by a translation and a rotation of the pin. Translation of the pin brings the cam into contact with the follower. Rotation of the pin, in accordance with the invention, also provides for operation of a cam that locks a clamp bar to prevent a conducting of the clamping procedure until the pin has been properly secured. Furthermore, the invention provides for a linkage between the trigger and a stapler dispensing pusher element of the staple cartridge which includes a removable link, insertion and extraction of the link depending on the state of the clamping mechanism so that no dispensing of staples can take place until the subject matter has been properly clamped.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. Apparatus for applying surgical fasteners to body tissue, comprising:
   a first jaw member comprising an anvil assembly;
   a second jaw member comprising a fastener holding assembly movably mounted relative to said anvil assembly;
   actuator means for moving the fastener holding assembly toward the anvil assembly to clamp the tissue to be fastened between the anvil assembly and the fastener holding assembly;
   pin means arranged for securing said first and second jaw members, said pin means providing a secured state when securing said first and second jaw members and an unsecured state when said first and second jaw members are not secured;
   activation means for ejecting fasteners from said fastener holding assembly in a direction toward said anvil assembly; and
   lockout means disposed to be driven by said pin means for inhibiting operation of both said actuator means and said activation means while in said unsecured state, said lockout means permitting operation of both said actuator means and said activation means during said secured state; wherein
   said actuator means includes a clamp bar and an adjustment lever for advancing said bar, for urging together said anvil assembly and said fastener holding assembly;
   said activation means includes a thrust bar, a trigger for advancing said thrust bar to eject a fastener, and an intermediate link for removably coupling said trigger to said thrust bar; and
   said intermediate link is movable to a first position for coupling said trigger to said thrust bar and a second position wherein said trigger and thrust bar are not coupled.

2. Apparatus for applying surgical fasteners to body tissue, comprising:
   a first jaw member comprising an anvil assembly;
   a second jaw member comprising a fastener holding assembly movably mounted relative to said anvil assembly;
   actuator means for moving the fastener holding assembly toward the anvil assembly to clamp the tissue to be fastened between the anvil assembly and the fastener holding assembly;
   pin means for securing said first and second jaw members, said pin means providing a secured state and an unsecured state;
   activation means for ejecting fasteners from said fastener holding assembly in a direction toward said anvil assembly; and
   lockout means driven by said pin means for inhibiting operation of said actuator means and said activation means while in said unsecured state;
   said lockout means permitting operation of said actuator means and said activation means during said secured state;
   wherein said actuator means includes a clamp bar and an adjustment lever for advancing said bar for urging together said anvil assembly and said fastener holding assembly;
   said activation means includes a thrust bar, a trigger for advancing said thrust bar to eject a fastener, and an intermediate link for connecting said trigger to said thrust bar; and
   wherein said lockout means is structured and arranged to retract said intermediate link from said thrust bar during said unsecured state, and to allow displacement of said intermediate link into contact with said thrust bar during said secured state.

3. Apparatus for applying surgical fasteners to body tissue, comprising:
- a first jaw member comprising an anvil assembly;
- a second jaw member comprising a fastener holding assembly movably mounted relative to said anvil assembly;
- actuator means for moving the fastener holding assembly toward the anvil assembly to clamp the tissue to be fastened between the anvil assembly and the fastener holding assembly;
- pin means for securing said first and second jaw members, said pin means providing a secured state and an unsecured state;
- activation means for ejecting fasteners from said fastener holding assembly in a direction toward said anvil assembly; and
- lockout means driven by said pin means for inhibiting operation of said actuator means and said activation means while in said unsecured state;
- said lockout means permitting operation of said actuator means and said activation means during said secured state;
- wherein said actuator means includes a clamp bar and an adjustment lever for advancing said bar for urging together said anvil assembly and said fastener holding assembly;
- said activation means includes a thrust bar, a trigger for advancing said thrust bar to eject a fastener, and an intermediate link for connecting said trigger to said thrust bar; and
- wherein said lockout means comprises a crank for blocking movement of said clamp bar during said unsecured state;
- said pin means includes a cam surface movable during a transition between said secured and said unsecured states; and
- said lockout means including a cam follower which rides upon said cam surface to operate said crank.

4. Apparatus according to claim 3, wherein
- said lockout means is structured and arranged to retract said intermediate link from said thrust bar during said unsecured state, and to allow displacement of said intermediate link into contact with said thrust bar during said secured state;
- said intermediate link is carried by said adjustment lever;
- a pivoting of said adjustment lever introducing a displacement of said clamp bar;
- said blocking of movement of said clamp bar by said crank also inhibiting said pivoting of said adjustment lever; and
- said pivoting of said adjustment lever being arranged such that said pivoting thereof is inhibited during said unsecured state and said pivoting of said adjustment lever during said secured state brings said intermediate link into contact with said thrust bar for operatively connecting said trigger to said thrust bar, to enable ejection of the fasteners.

5. Apparatus for applying surgical fasteners to body tissue comprising:
- a frame, a first jaw and a second jaw facing each other and supported by said frame, said first jaws comprising an anvil, said second jaw being configured for holding a fastener cartridge and allowing translation of said cartridge toward said first jaw to provide for a clamping of body tissue to be fastened;
- pin means for bridging a gap between said first jaw and said second jaw to secure said jaws against loss of the body tissue, said pin means including a pin slidably mounted within said second jaw and lockable to said first jaw upon rotation of said pin, said pin means providing a secured state and an unsecured state;
- clamping means including a clamp bar supported by said frame for urging said cartridge toward said anvil;
- thrust means including a thrust bar supported by said frame for activating said cartridge to dispense fasteners in a direction toward said anvil; and
- lockout means driven by said pin means for inhibiting operation of said clamping means and operation of said thrust means during said unsecured state, said lockout means permitting operation of said clamping means and said thrust means during said secured state; and wherein
- said lockout means includes first lock means for inhibiting operation of said clamping means, and said pin means includes a cam and a follower operative upon rotation of said pin, said cam being connected to said first lock means by said follower for unlocking said clamping means upon rotation of said pin; and
- said lockout mean comprises second lock means for inhibiting operation of said thrust means and operable in response to motion of said clamp bar, a movement of said clamp bar towards said anvil allowing operation of said second lock means to enable operation of said thrust bar, retraction of said clamp bar disabling operation of said thrust bar.

6. Apparatus according to claim 5, wherein said second lock means comprises a removable link couplable to said thrust bar for activating said thrust bar, said removable link being retracted from an operative position during said unsecured state and being insertable into an operative position during said secured state.

7. Apparatus for applying surgical fasteners to body tissue, comprising:
- a first jaw member comprising an anvil assembly;
- a second jaw member comprising a fastener holding assembly movably mounted relative to said anvil assembly;
- actuator means for moving the fastener holding assembly toward the anvil assembly to clamp the tissue to be fastened between the anvil assembly and the fastener holding assembly;
- pin means arranged for securing said first and second jaw members, said pin means providing a secured state when securing said first and second jaw members and an unsecured state when said first and second jaw members are not secured;
- activation means for ejecting fasteners from said fastener holding assembly in a direction toward said anvil assembly; and
- lockout means disposed to be driven by said pin means for inhibiting operation of both said actuator means and said activation means while in said unsecured state, said lockout means permitting operation of both said actuator means and said activation means during said secured state;
- wherein said lockout means is mounted separate from said pin means and is mounted to be directly drivable by said pin means in response to movement of said pin means from said unsecured state to said secured state; and wherein said lockout means is structured and arranged to be cammed by said pin means, to permit operation of both said actuation and activation means.

8. Apparatus for applying surgical fasteners to body tissue, comprising:
- a first jaw member comprising an anvil assembly;
- a second jaw member comprising a fastener holding assembly movably mounted relative to said anvil assembly;
- actuator means for moving the fastener holding assembly toward the anvil assembly to clamp the tissue to be fastened between the anvil assembly and the fastener holding assembly;
- pin means arranged for securing said first and second jaw members, said pin means providing a secured state when securing said first and second jaw members and an unsecured state when said first and second jaw members are not secured;
- activation means for ejecting fasteners from said fastener holding assembly in a direction toward said anvil assembly; and
- lockout means disposed to be driven by said pin means for inhibiting operation of both said actuator means and said activation means while in said unsecured state, said lockout means permitting operation of both said actuator means and said activation means during said secured state;
- wherein said lockout means is mounted separate from said pin means and is mounted to be directly drivable by said pin means in response to movement of said pin means from said unsecured state to said secured state; and
- wherein said lockout means is mounted to be drivable in a different direction than a direction of movement of said pin means from said unsecured state to said secured state.

9. Apparatus according to claim 8, wherein said lockout means is disposed to be driven by rotation of said pin means.

10. Apparatus for applying surgical fasteners to body tissue, comprising:
- a first jaw member comprising an anvil assembly;
- a second jaw member comprising a fastener holding assembly movably mounted relative to said anvil assembly;
- actuator means for moving the fastener holding assembly toward the anvil assembly to clamp the tissue to be fastened between the anvil assembly and the fastener holding assembly;
- pin means arranged for securing said first and second jaw members, said pin means providing a secured state when securing said first and second jaw members and an unsecured state when said first and second jaw members are not secured;
- activation means for ejecting fasteners from said fastener holding assembly in a direction toward said anvil assembly; and
- lockout means disposed to be driven by said pin means for inhibiting operation of both said actuator means and said activation means while in said unsecured state, said lockout means permitting operation of both said actuator means and said activation means during said secured state;
- wherein said lockout means is disposed to directly inhibit operation of both said actuator mean and said activation means while in said unsecured state;
- wherein said lockout means is mounted separate from said pin means and is mounted to be directly drivable by said pin means in response to movement of said pin means from said unsecured state to said secured state; and
- wherein said lockout means is structured and arranged to be cammed by said pin means, to permit operation of both said actuation and activation means.

11. Apparatus for applying surgical fasteners to body tissue, comprising:
- a first jaw member comprising an anvil assembly;
- a second jaw member comprising a fastener holding assembly movably mounted relative to said anvil assembly;
- actuator means for moving the fastener holding assembly toward the anvil assembly to clamp the tissue to be fastened between the anvil assembly and the fastener holding assembly;
- pin means arranged for securing said first and second jaw members, said pin means providing a secured state when securing said first and second jaw members and an unsecured state when said first and second jaw members are not secured;
- activation means for ejecting fasteners from said fastener holding assembly in a direction toward said anvil assembly; and
- lockout means disposed to be driven by said pin means for inhibiting operation of both said actuator means and said activation means while in said unsecured state, said lockout means permitting operation of both said actuator means and said activation means during said secured state;
- wherein said lockout means is disposed to directly inhibit operation of both said actuator means and said activation means while in said unsecured state;
- wherein said lockout means is mounted separate from said pin means and is mounted to be directly drivable by said pin means in response to movement of said pin means from said unsecured state to said secured state; and
- wherein said lockout means is mounted to be drivable in a different direction than a direction of movement of said pin means from said unsecured state to said secured state.

12. Apparatus according to claim 11, wherein said lockout means is disposed to be driven by rotation of said pin means.

* * * * *